US006439236B1

(12) United States Patent
Porter et al.

(10) Patent No.: US 6,439,236 B1
(45) Date of Patent: Aug. 27, 2002

(54) METHODS FOR INDUCING ATRIAL AND VENTRICULAR RHYTHMS USING ULTRASOUND AND MICROBUBBLES

(75) Inventors: Thomas R. Porter; Feng Xie, both of Omaha, NE (US)

(73) Assignee: The Board of Regents of the University of Nebraska, Lincoln, NE (US)

(*) Notice: Subject to any disclaimer, the term of this patent is extended or adjusted under 35 U.S.C. 154(b) by 0 days.

(21) Appl. No.: 09/426,378

(22) Filed: Oct. 25, 1999

(51) Int. Cl.[7] .............................................. A61B 19/00
(52) U.S. Cl. ......................... 128/898; 604/23; 424/9.52
(58) Field of Search .............................. 601/2; 607/152; 424/9.52, 94.63, 94.64, 9.5; 604/23, 24, 26, 27, 28, 290, 20, 500, 506, 507, 511; 600/431, 508–528, 437–461, 9–17; 128/898; 530/363, 427

(56) References Cited

U.S. PATENT DOCUMENTS

| | | | |
|---|---|---|---|
| 4,718,433 A | | 1/1988 | Feinstein |
| 5,560,364 A | * | 10/1996 | Porter .................... 128/662.02 |
| 5,567,415 A | * | 10/1996 | Porter ......................... 424/9.52 |
| 5,685,310 A | * | 11/1997 | Porter .................... 128/662.02 |
| 5,695,740 A | * | 12/1997 | Porter ......................... 424/9.52 |
| 5,701,899 A | * | 12/1997 | Porter .................... 128/662.02 |
| 6,045,118 A | * | 4/2000 | Ostensen .................... 424/9.52 |
| 6,139,819 A | * | 10/2000 | Unger et al. ................ 424/9.52 |
| 6,231,834 B1 | * | 5/2001 | Unger et al. ................ 424/9.51 |

FOREIGN PATENT DOCUMENTS

| | | | | |
|---|---|---|---|---|
| WO | WO 93/05819 | 4/1993 | .......... | A61K/49/00 |
| WO | WO 95/23615 | 9/1995 | .......... | A61K/49/00 |
| WO | WO 99/61058 | 12/1999 | | |

OTHER PUBLICATIONS

Xinfang, Wang; Jiaen, Wang; Youzhen, Huang; Chongde, Cai; Contrast Echocardiography with Hydrogen Peroxide, I. Experimental Study, 1979, Chinese Medical Journal, 92/9, 595–599.*

"Mycardial perfusion abnormalities during low–dose dobutamine after coronary reperfusion can be demonstrated with intravenous perfluorocarbon–exposed sonicated dextrose albumin ultrasound contrast", by Thomas R. Porter, MD, Feng Xie, MD, Alan Kricsfeld, BA, Ubeydullah Deligonul, MD, Karen Kilzer, RT, and David Kricsfeld; Omaha, NE; University of Nebraska Medical Center Sep. 6, 1995.

"Visually Discernible Myocardial Echocardiographic Contrast After Intravenous Injection of Sonicated Dextrose Albumin Microbubbles Containing High Molecular Weight, Less Soluble Gases," Thomas R. Porter, MD, FACC and Feng Xie, MD; Omaha, NE; American College of Cardiology; 1995.

"Transthoracic Ultrasound and Microbubble Induced Atrial and Ventricular Arrhythmias: Incidence and Potential Mechanisms," Thomas R. Porter, Feng Xie, David Kricsfeld, Huagul Li; University of Nebraska Medical Center; Omaha, NE.

(List continued on next page.)

Primary Examiner—David J. Isabella
Assistant Examiner—Urmi Chattopadhyay
(74) Attorney, Agent, or Firm—McKee Voorhees & Sease, P.L.C.

(57) ABSTRACT

A new and improved method for inducing or pacing atrial and ventricular arrhythmias in animals Embodiments of the invention involve using microbubbles enhanced with an insoluble gas in combination with low frequency ultrasound for its pacing activity. The methods and compositions can be used to pace patients, convert patients out of atrial fibrillation, and as a diagnostic to assess a patient's risk for arrhythmias.

38 Claims, 1 Drawing Sheet

OTHER PUBLICATIONS

Figure 1:
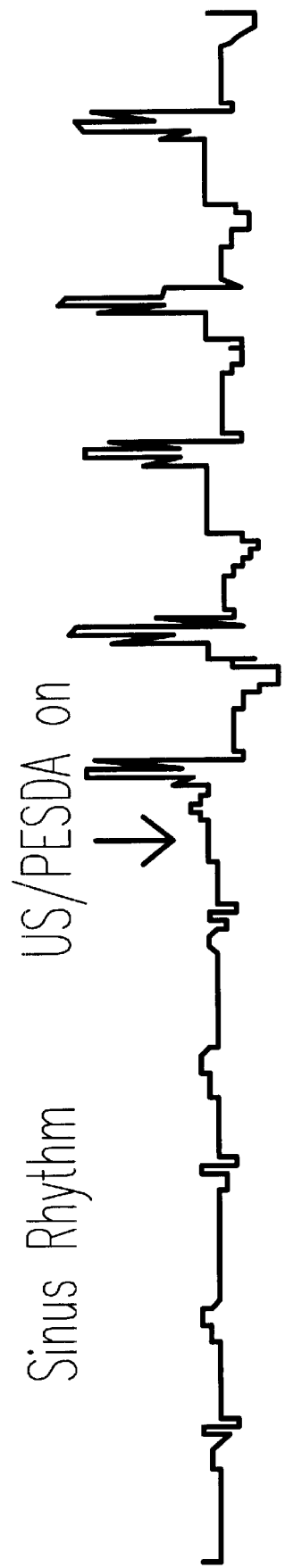

Porter, "The Mechanism and Clinical Implication of Improved Left Ventricular Videointensity Following Intravenous Injection of Multi–Fold Dilutions of Albumin With Dextrose", *Int. J. Card Imaging,* Jun. 1995, vol. 11, No. 2, pp. 117–125, XP000590839.

Xie F. et al., "Acute Myocardial Ischemia and Reperfusion Can be Visually Identified Non–Invasively with Intravenous Perfluoropropane–Enhanced Sonicated Dextrose Albumin Ultrasound Contrast", Abstract No. 2989, 67th Scientific Sessions of the American Heart Assoc., Dallas, TX, USA, Nov. 14–17, 1994, Circulation, 1994, vol. 90, No. 4 part 2, p. 1555, XP000577054.

Porter, et al., "Echocardiographic Detection of Residual Coronary Flow Abnormalities and Stenosis Severity After Coronary Reperfusion Using Intravenous Perfluoropropane–Enhanced Sonicated Dextrose Albumin", Abstract No. 955–60, 44th Annual Scientific Session of the American College of Cardiology, New Orleans, LA, USA, Mar. 19–22, 1995. In: *Journal of the American College of Cardiology,* Spec. Issue, p. 205A., XP000577058.

Kricsfeld et al, "Detection of Regional Perfusion Abnormalities During Adenosine Stress Echocardiography Using Intravenous Perfluoropropane–Enhanced Sonicated Dextrose Albumin", Abstract No. 703–2, 44th Annual Scientific Session of the American College of Cardiology, New Orleans, LA, USA, Mar. 19–22, 1995. In: *Journal of the American College of Cardiology,* Spec. Issue, p. 38A, XP000577057.

Porter, et al, "Multifold Sonicated Dilutions of Albumin with Fifty Percent Dextrose Improve Left Ventricular Contrast Videonintensity After Intravenous Injection in Human Beings", abstract, *J. Am Soc. Echocardiogr,* Sep.–Oct. 1994, vol. 7, No. 5, pp. 465–471, XP000590864.

Xie, et al, "Perfluoropropane Enhanced Sonicated Dextrose Albumin Produces Visually Apparent Consistent Myocardial Opacification With Physiologic Washout and Minimal Hemodynamic Changes Following Venous Injection", Apstract No. 362, 67th Scientific Sessions of the American Heart Association, Dallas, TX, USA, Nov. 14–17, 1994. In: Circulation, 1994, vol. 90, No. 4 Part 2, p. 269, XP000577055.

Porter, et al, "Visually Discernible Myocardial Echocardiographic Contrast After Intravenous Injection of Sonicated Dextrose Albumin Microbubbles Containing High Molecular Weight, Less Soluble Gases", abstract, *J Am Coll Cardiol,* Feb. 1995, vol. 25, No. 2, pp. 509–515, XP000590866.

Porter, et al, Noninvasive Identification of Acute Myocardial Ischemia and Reperfusion With Contrast Ultrasound Using Intravenous Perfluoropropane–Exposed Sonicated Dextrose Albumin, abstract, *J Am Coll Cardiol,* Jul. 1995, vol. 26, No. 1, pp. 33–40, XP000590865.

* cited by examiner

METHODS FOR INDUCING ATRIAL AND VENTRICULAR RHYTHMS USING ULTRASOUND AND MICROBUBBLES

GRANT REFERENCE

Work for this invention was funded in part by a federal grant from NIH, Grant #MWT17-076-92201. The Government may have certain rights in this invention.

FIELD OF THE INVENTION

This invention relates to a new and improved method for inducing or pacing atrial and ventricular arrhythmias in animals. The methods and compositions of the invention can be used to pace patients, convert patients out of atrial fibrillation, convert patients with ventricular rhythm disturbances and even as a diagnostic to assess a patients risk for arrhythmias.

BACKGROUND OF THE INVENTION

Normal sinus rhythm of the heart begins with the sinoatrial node (or 'SA node') generating a depolarization wave front. The impulse causes adjacent myocardial tissue cells in the atria to depolarize, which in turn causes adjacent myocardial tissue cells to depolarize. The depolarization propagates across the atria, causing the atria to contract and empty blood from the atria into the ventricles. The impulse is next delivered via the atrioventricular note (or 'AV node') and the bundle of HIS (or 'HIS bundle') to myocardial tissue cells of the ventricles. The depolarization of these cells propagates across the ventricles, causing the ventricles to contract.

This conduction system results in the organized sequence of myocardial contraction leading to a normal heartbeat.

Sometimes aberrant conductive pathways develop in heart tissue, which disrupt the normal path of depolarization events. For example, anatomical obstacles in the atria or ventricles can disrupt the normal propagation of electrical impulses. These anatomical obstacles (called 'conduction blocks') can cause the electrical impulse to degenerate into several circular wavelets that circulate about the obstacles. These wavelets, called 'reentry circuits,' disrupt the normal activation of the atria or ventricles. As a further example, localized regions of ischemic myocardial tissue may propagate depolarization events slower than normal myocardial tissue. The ischemic region, also called a 'slow conduction zone,' creates errant, circular propagation patterns, called 'circus motion.' The circus motion also disrupts the normal depolarization patterns, thereby disrupting the normal contraction of heart tissue.

The aberrant conductive pathways create abnormal, irregular, and sometimes life-threatening heart rhythms, called arrhythmias. An arrhythmia can take place in the atria, for example, as in atrial tachycardia or atrial flutter. The arrhythmia can also take place in the ventricle, for example, as in ventricular tachycardia.

Atrial fibrillation is one of the most common arrhythmias, and is usually associated with patients of an increased age. About ten percent of patients who are at least 65 years old present with atrial fibrillation. Atrial fibrillation is associated with troublesome symptoms for patients, and also has a significantly adverse influence on the cardiac function. It is also well known that there is an increased risk of embolic events following atrial fibrillation. Accordingly, the increased heart rate associated with atrial fibrillation needs to be controlled. The primary current treatments for atrial fibrillation as the use of anti-arrhythmic drugs, or electric cardioversion. Use of anti-arrhythmic drugs is often associated with potential proarrhythmic effects, especially in patients with already compromised ventricular function. Such a proarrhythmic effect can outweigh the potential benefit of drug administration. On the other hand, transthoracal electrical cardioversion is an extreme therapy, requiring a discharge energy in the range of 50 to 360 Joules. This treatment requires general anesthesia, and serious side effects may occur as a result. Often patients receive superficial skin burns at the site of the shock. Additionally distressing is the fact that there are a substantial number of patients who may not be cardioverted externally, requiring invasive transvenous cardioversion.

As can be seen, a need exists in the art for a method of inducing or pacing atrial or ventricular rhythms which is noninvasive, safe and nontoxic to patients.

It is an object of the present invention to provide a safe nontoxic microbubble composition and method which can be used to induce cardiac rhythms in animals.

It is yet another object to provide a method of inducing or pacing cardiac rhythms which is noninvasive and does not require anesthetic.

These and other objects of the invention will become apparent from the description of the invention which follows.

SUMMARY OF THE INVENTION

According to the invention a cardiac rhythm therapy is provided which is noninvasive, painless and non toxic. The therapy involves the combination of low frequency transthoracic ultrasound and a pharmaceutical composition. The composition comprises microbubbles of a diameter of about 0.1 to 10 microns, the interior of which has been enhanced with an insoluble gas such as fluorocarbon gas, helium or sulfur hexafluoride and which gas is encapsulated in a protein-coated shell. The invention uses agents and methods traditionally used in ultrasound imaging and as such provides a means for visualization of the heart as the rhythm is induced. Quite unexpectedly it was found that the insoluble gas microbubbles of the invention in combination with low frequency ultrasound act themselves inducing, or pacing atrial and ventricular rhythms in animals, and induction can be manipulated by directing the ultrasound to either the atrium or ventricle. This strategy can be used in any of a number of cardiac rhythm strategies. For example it can be used to non-invasively convert patients to a regular rhythm from atrial fibrillation. It could also be used as a diagnostic to identify patients who are vulnerable to ventricular rhythm disturbances. These are just two examples of potential uses for this strategy and are not intended to limit the invention in any way. Other uses are described and exemplified herein and will be obvious to those of skill in the art from the teachings herein.

DETAILED DESCRIPTION OF THE FIGURES

FIG. 1 is an electrocardiogram illustrating the induction of normal sinus rhythm through application of microbubbles and ultrasound according to the invention.

DETAILED DESCRIPTION OF THE INVENTION

Ultrasonic imaging has long been used as a diagnostic tool to aid in therapeutic procedures. It is based on the principle that waves of sound energy can be focused upon an area of interest and reflected to produce an image. Generally an ultrasonic transducer is placed on a body surface overlying the area to be imaged and ultrasonic energy, produced by generating and receiving sound waves, is transmitted. The ultrasonic energy is reflected back to the transducer where it is translated into an ultrasonic image. The amount of characteristics of the reflected energy depend upon the acoustic properties of the tissues, and contrast agents which are echogenic are preferably used to create ultrasonic energy in the area of interest and improve the imaging received. For a discussion of contrast echographic instrumentation, see, DeJong and, "Acoustic Properties of Ultrasound Contrast Agents", CIP-GEGEVENS KONINKLIJKE BIBLIOTHEEK, DENHAG (1993), pp. 120 et seq.

Contrast echocardiography has been used to delineate intracardiac structures, assess valvular competence, and demonstrate intracardiac shunts. Myocardial contrast echocardiography has been used to measure coronary blood flow reserve in humans. Myocardial contrast echocardiography has been found to be a safe and useful technique for evaluating relative changes in myocardial perfusion and delineating areas at risk.

Ultrasonic vibration has also been used in the medical field to increase the absorption of various medicaments. For example in Japanese Patent Kokai number 115591/1977 discloses that percutaneous absorption of a medicament is enhanced by applying an ultrasound vibration. U.S. Pat. Nos. 4,953,565 and 5,007,438 also disclose a technique of percutaneous absorption of medicaments by the aid of ultrasonic vibration. U.S. Pat. No. 5,315,998 discloses a booster for drug therapy comprising microbubbles in combination ultrasonic energy to allow the medicament to diffuse and penetrate at the site of interest.

Quite surprisingly applicant has demonstrated that a microbubble composition in combination with ultrasound therapy can act as an inducer or pacer for atrial and ventricular arrhythmias in animals.

According to the invention a microbubble composition given intravenously in combination with ultrasound continuous wave of 1 mega hertz ultrasound probe as opposed to an imaging probe will induce either ventricular, junctional, or atrial paced beats. The duration of the paced rhythm is dependent on microbubble concentration in the left ventricular cavity and may be programmed by the infusion rate of microbubble composition. The type of beat that is induced (ventricular, junctional, or atrial) is dependent on where the ultrasound beam is directed. For example if the beam is directed towards the atrium atrial beats are induced. This inducing action is not observed with either ultrasound or microbubble composition alone.

The pharmaceutical composition of the invention comprises a liquid containing microbubbles of an insoluble gas having a diameter of 0.1 to 10 microns. The microbubbles are formed by entrapping microspheres of a gas into a liquid. The microbubbles are made of various gases preferably inert gases as xenon, krypton, argon, neon, helium, or fluorocarbon gases. The liquid includes any liquid which can form microbubbles. Generally any inert gas can be used. It must be gaseous at body temperature and be nontoxic. The gas must also form stable microbubbles of average size of between about 0.1 and 10 microns in diameter when the pharmaceutical composition is sonicated to form microbubbles. Generally perfluorocarbon gases such as perfluoromethane, perfluoroethane, perfluoropropane, perfluorobutane, perfluoropentane are preferred. Of these gases, perfluoropropane and perfluorobutane are especially preferred because of their demonstrated safety for intraocular injection in humans. They have been used in human studies for intraocular injections to stabilize retinal detachments (Wong and Thompson, Opthamology 95:609–613). Treatment with intraocular perfluoropropane is considered to be the standard of care for treatment of this disorder. The gases must also have a diffusion coefficient and blood solubility lower than nitrogen or oxygen which diffuse once in the internal atmosphere of the blood vessel.

Other inert gases such as sulfur hexafluoride are also useful in the invention provided they have a diffusion coefficient and blood solubility lower than nitrogen or oxygen. The agent of the invention is formulated in a pharmaceutically effective dosage form for peripheral administration to the host in conjunction with ultrasound therapy. Generally such host is a human host, although other mammalian hosts such as canine or equine can also be subject to this therapy.

In a preferred embodiment the pharmaceutical liquid composition of the invention uses a liquid wherein the microbubbles are stabilized by a filmogenic denaturable protein coating. Suitable proteins include naturally occurring proteins such as albumin, human gamma globulin, human apotransferin, Beta lactose and urease. The invention preferably employs a naturally occurring protein but synthetic proteins may also be used. Particularly preferred is human serum albumin.

It is also preferred to use an aqueous solution containing a mixture of a pharmaceutically accepted saccharide e.g., dextrose, in combination with the earlier described protein. In a most preferred embodiment the pharmaceutical liquid composition of the invention is the sonicated mixture of commercially available albumin (human), U.S.P. solution (generally supplied as 5% or 25% by weight sterile aqueous solutions), and commercially available dextrose, U.S.P. for intravenous administration. The mixture is sonicated under ambient conditions i.e. room air temperature and pressure and is perfused with an insoluble gas (99.9% by weight) during sonication.

In a most preferred embodiment the pharmaceutical liquid composition includes a two-fold to eight-fold dilution of 5% to 50% by weight of dextrose and a 2% to 10% by weight of human serum albumin. Exemplary of other saccharide solutions of the invention are aqueous monosaccharide solution (e.g. having the formula $C_6H_{12}O_6$ such as the hexose sugars, dextrose or fructose or mixtures thereof), aqueous disaccharide solution (e.g such as sucrose, lactose or maltose or mixtures thereof), or aqueous polysaccharide solution (e.g. soluble starches having the formula $C_6H_{10}O_5$ (n) wherein n is a whole number integer between 20 and about 200 such as amylase or dextran or mixtures thereof.

The microbubbles are formed by sonication, typically with a sonicating horn. Sonication by ultrasonic energy causes cavitation within the dextrose albumin solution at sites of particulate matter or gas in the fluid. These cavitation sites eventually resonate and produce small microbubbles (about 7 microns in size) which are non-collapsing and stable. In general, sonication conditions which produce concentrations of greater than about $4 \times 10^8$ m of between about 5 and about 6 micron microbubbles are preferred. Generally the mixture will be sonicated for about 80 seconds, while being perfused with an insoluble gas.

A second method of preparation includes hand agitating 15±2 ml of sonicated dextrose albumin with 8±2 ml of perfluorocarbon gas prior to sonication. Sonication then proceeds for 80±5 seconds. Generally the pharmaceutical liquid composition is injected into so that it will perfuse the heart and then ultrasound is applied.

These microbubble sizes are particularly ideal since a microbubble must have a mean diameter of less than 10 microns and greater than 0.1 to be sufficient for transpulmonary passage, and must be stable enough to prevent significant diffusion of gases within the microbubble following intravenous injection and during transit to the heart. The method preferred for practicing the cardiac rhythm therapy of the invention involves obtaining a pharmaceutical liquid agent of the invention, introducing said agent into a host by intravenous injection, intravenously (i.v. infusion), percutaneously or intramuscularly. Injection is similar to the practices used for ultrasonic imaging of the heart. Next ultrasound is applied thereto using a suitable Doppler or ultrasound echo apparatus so that the field of ultrasound encompasses the heart.

The desired ultrasound is applied by conventional ultrasonic devices which can supply an ultrasonic signal of 20 Khz to several Mhz and is applied at ranges lower than that used for diagnostic ultrasound, which is typically from about 3 to about 5 Mhz. Instead ultrasound is applied at much lower frequencies, preferably at frequencies of 20 Khz to 2.5 Mhz and most preferably on the order of about 1 Mhz. An ultrasound probe may be used instead of an imaging probe. The ultrasound is preferably applied at a peak negative pressure greater than 1 megapascal and in a continuous wave mode. The ultrasound will preferably have a high mechanical index of approximately 0.4 to 2.0 with a most preferred mechanical index of 0.7. The mechanical index is the peak negative pressure divided by the square foot of the transmitted frequency. The ultrasound is administered for a length of time that the user wants the rhythm disturbance to last which could range from 1 second to 10 days or even longer.

In the most preferred embodiment the agent of the invention is a perfluorocarbon enhanced sonicated dextrose albumin solution comprised of a sonicated three-fold dilution of 5% human serum albumin with 5% dextrose. During sonication, the solution is perfused with perfluorocarbon gas for about 80 seconds which lowers the solubility and difusivity of the microbubble gas. The resulting microbubbles are concentrated at room temperature for at least about 120±5 minutes wherein the excess solution settles in the sonicating syringe. The excess solution is expelled and the concentrated microbubbles are transferred to a sterile syringe and injected parenterally into a mammal.

Methods of ultrasonic imaging in which microbubbles formed by sonicating an aqueous protein solution are injected into a mammal to alter the acoustic properties of a predetermined area which is then ultrasonically scanned to obtain an image for use in medical procedures is well known. For example see U.S. Pat. No. 4,572,203, U.S. Pat. No. 4,718,433 and U.S. Pat. No. 4,774,958, the contents of each of which are incorporated herein by reference.

It is the use of these types of contrast agents as a pharmaceutical composition and application of ultrasound as an arrhythmia therapy that is the novel improvement of this invention. According to the invention, it was shown that treatment with perfluorocarbon exposed sonicated dextrose albumin microbubbles and subsequent application of ultrasound induced either centricular or atrial arrhythmias. The type of arrhythmia induced was programmed by directing the transthoracic beam towards the atrium or ventricle.

This is particularly significant as the microbubble ultrasound therapy is noninvasive, painless, nontoxic and can be used for persons who cannot otherwise use traditional arrhythmic therapies. The protein substance surrounding the microbubbles such as human serum albumin is easily metabolized within the body and excreted and hence is not harmful to the human body. Further gas trapped within the microbubbles is extremely small and is easily dissolved in blood fluid, perfluoropropane and perfluorobutane have long been known to be safe in humans. Both have been used in humans for intra ocular injections to stabilize retinal detachments. Wong and Thompson, Opthalmology 95:609–613. Thus the arrhythmic agents of the invention are extremely safe and nontoxic for patients.

This type of therapy can be used in any therapy designed to alter or induce cardiac rhythm. Some non-limiting examples include the following: pacing of patients noninvasively who have serious bradyarrhythmias (slow heart rates). Currently this requires a pacemaker be inserted into the heart or the patient receive electrical shock waves; converting patients out of atrial fibrillation. This is a common rhythm disturbance that several thousands of patients every year. To convert patients now, it requires that they get an electrical shock under anesthesia. Since the application of ultrasound is only associated with some warming of the skin over the heart, this could be an alternative for patients; converting patients with life threatening ventricular rhythm disturbances. This also requires an electrical shock; assessing someone's risk for having a dangerous ventricular rhythm disturbance. Currently this requires an invasive study called an electrophysiologic study. Using the methods and compositions of the invention one could potentially determine this risk with a non-invasive ultrasound pacing study and PESDA.

The following examples are for illustration purposes only and are not intended to limit this invention in any way. Those of skill in the art will appreciate that certain parameters may be optimized for a particular application. These optimized strategies or expedients are intended to be within the scope of the invention. The following example demonstrates the effect of the pharmaceutical compositions and therapy of the invention. All parts and percentages are by weight unless otherwise, all dilutions are by volume.

EXAMPLES

Preparation of Microbubble Agent

Albumin (human) USP, 5% solution (hereinafter referred to as "albumin") and dextrose USP, 5% solution (hereinafter referred to as "dextrose") were obtained from a commercial source. The sonicating system used for sonication was a Heat System Ultrasonic Processor Model XL2020 (Heat Systems Inc., Farmingdale, New York). The ½ inch horn transducer was a resonating piezoelectric device. The ½ inch sonicating horn tip was sterilized prior to each sonication.

Sonication of Samples

Sixteen milliliter aliquots of albumin diluted 1:3 with dextrose were drawn up into a 35 cc "Monoject" syringe (Becton Dickinson and Company, Rutherford, N.J.) and sonicated for 80±1 seconds. The "Leur-Lok" of the 35 milliliter syringe was then attached to a stopcock. After mixing the dextrose albumin solution by hand for about 7 to about 10 seconds, the plunger was removed from the top of the syringe. The sterile sonicating horn was then lowered into the open end of the syringe until at the surface of the albumin-dextrose solution. The solution was placed at the horn tip and manually held at this position while continuously sonicating at a frequency of 20,000 Hz and a power output of 210 W for 80±1 seconds to form a stable microbubble solution.

Gas Perfusion of Samples

A second method of preparation includes hand agitating 15±2 ml of sonicated dextrose albumin with 8±2 ml of perfluorocarbon gas prior to sonication. Sonication then proceeds for 80±5 seconds. Generally the pharmaceutical liquid composition is injected into the animal so that the composition will perfuse the heart and then ultrasound is applied.

The dextrose albumin mixture was exposed to either perfluoropropane or perfluorobutane gas (Commercial Grade, 99.9% by weight) by hand agitating 15±2 ml of sonicated dextrose albumin with 8±2 ml of perfluorocarbon gas prior to sonication. The perfluorocarbon/dextrose-albumin mixture was then sonicated for 80±5 seconds. The total volume of perfluorocarbon-enhanced sonicated dextrose albumin produced with this formulation was 25±2 milliliters. These samples were then used for intravenous injection.

Microbubble Analysis

Microbubble size and purity was determined using hemocytometry. Microscopic inspection of the microbubbles was performed to determine if any coalescent microbubbles were present in the solution. Microbubble concentration was determined using a Coulter Counter. The microbubble pharmaceutical agent was rejected for use if any of the following conditions are present: the mean microbubble size was 4.0 to 6.0 microns; coalesced microbubbles or strands were detected by light microscopy; or the mean microbubble concentration was less than $0.8 \times 10^9$ or greater than $1.5 \times 10^9$ microbubble/milliliter. The sample was also rejected if the number of microbubbles greater than 10 microns in the sample was greater than 4%.

All samples were stored in 35 milliliter syringes until time of injection. All solutions were given within 36 hours of production. All samples were prepared in a laminar flow hood.

Cardiac Rhythm Induction

Transthoracic ultrasound can induce premature ventricular contractions following intravenous microbubble injections when using a high mechanical index. While not wishing to be bound by any theory it is hypothesized that ultrasound-microbubble induced arrhythmias were a result of localized cavitation within the field of insonation, and could therefore be programmed to occur in both atrium and ventricle. In 26 pigs, we monitored electrocardiographic changes during either ultrasound alone (1 Megahertz; Mechanical index=0.7); intravenous perfluorocarbon exposed sonicated dextrose albumin (perfluorobutane) microbubbles alone, or intravenous perfluorocarbon exposed sonicated dextrose albumin plus ultrasound insonifying either the left ventricular or atrial regions. Surface EKG and quadripolar right atrial tracings recorded the location of any induced arrhythmias.

One MHz ultrasound plus perfluorocarbon exposed sonicated dextrose albumin induced either left ventricular or atrial arrhythmias at peak concentration (longest duration 26 beats following 109 of 119 injections (91.5%) FIG. 1). Brief episodes of atrial fibrillation were also induced. The type of arrhythmia (left ventricular or atrial) could be programmed by directing the transthoracic ultrasound beam toward the ventricle or atrium. Arrhythmias were never observed with intravenous PESDA alone, 1 MHz ultrasound alone, or with diagnostic ultrasound (1.7 MHz, 0.7 mechanical index) in the presence of microbubbles. These data indicate that transthoracic ultrasound plus a microbubbles composition is capable of stimulating left ventricular and atrial arrhythmias. The threshold for induction is dependent on microbubble concentration and ultrasound frequency.

What is claimed is:

1. A method of inducing or pacing atrial and/or ventricular rhythms in animals comprising the steps of:
    introducing a microbubble composition to said animal by intravenous injection so that the heart of said animal becomes perfused with said microbubble composition, said microbubble composition comprising a plurality of gas filled microbubbles with a diameter of from about 0.1 to about 10 microns and a pharmaceutically acceptable carrier, and in combination;
    applying a low frequency, high mechanical index ultrasound to said animal so that an ultrasound field is directed to the heart, or a portion thereof to induce paced beats.

2. The method of claim 1 wherein said ultrasound is applied at a frequency of 2.5 Mhz or less.

3. The method of claim 1 wherein said ultrasound is applied at a frequency of 1 Mhz.

4. The method of claim 1 wherein said ultrasound is applied at a mechanical index of 0.7.

5. The method of claim 1 wherein said ultrasound is applied in continuous wave mode.

6. The method of claim 1 wherein said ultrasound is directed to the ventricle of said heart.

7. The method of claim 1 wherein said ultrasound is directed to the atrium of said heart.

8. The method of claim 1 wherein said gas is an insoluble gas.

9. The method of claim 8 wherein said insoluble gas is selected from the group consisting of perfluoromethane, perfluoroethane, perfluoropropane, perfluorobutane and perfluoropentane.

10. The method of claim 9 wherein said insoluble gas is perfluorobutane.

11. The method of claim 9 wherein said insoluble gas is perfluoropropane.

12. The method of claim 1 wherein said microbubbles are protein coated.

13. The method of claim 12 wherein said protein coated microspheres are albumin coated microbubbles.

14. The method of claim 1 wherein said carrier is a 5% solution of dextrose.

15. The method of claim 1 further comprising the following steps:
    mixing an aqueous solution comprising from about 2% to about 10% by weight of human serum albumin diluted about two fold to about eight fold with from about 5% to about 50% by weight dextrose; and
    exposing said solution to a sonication horn to generate stable microbubbles from about 0.1 to bout 10 microns in diameter, to create said microbubble composition.

16. The method of claim 15 wherein said dilution of albumin with dextrose is a 3-fold dilution.

17. The method of claim 15 wherein said human serum albumin is a 5% by weight solution.

18. The method of claim 15 wherein said dextrose is a 5% by weight solution.

19. The method of treatment for use in inducing or pacing arrhythmias in animals comprising:

(a) obtaining a pharmaceutical composition which consists essentially of:
   a solution of stable microbubbles approximately 0.1 to about 10 microns in
   diameter, and a pharmaceutically acceptable carrier;
(b) introducing said microbubble composition to the heart of said animal; and
(c) exposing said microbubble composition and said heart to a transthoracic ultrasound field for a time sufficient to stimulate arrhythmia.

20. The method of claim 19 wherein said ultrasound is applied at a frequency of 2.5 Mhz or less.

21. The method of claim 19 wherein said ultrasound is applied at a frequency of 1 Mhz.

22. The method of claim 19 wherein said ultrasound is applied at a mechanical index of 0.7.

23. The method of claim 19 wherein said ultrasound is applied in continuous wave mode.

24. The method of claim 19 wherein said ultrasound is directed to the ventricle of said heart.

25. The method of claim 19 wherein said ultrasound is directed to the atrium of said heart.

26. The method of claim 19 wherein said step of introducing said agent to said heart is by intravenous injection.

27. The method of claim 19 wherein said dextrose is a 5% solution.

28. The method of claim 19 wherein said protein coated microbubbles are albumin coated microbubbles.

29. The method of claim 19 further comprising the following steps:
   mixing aqueous solution comprising from about 2% to about 10% by weight of human serum albumin diluted about two fold to about eight fold with from about 5% to about 50% by weight dextrose; and
   exposing said solution to a sonication horn to create cavitation at particulate sites in said solution generating stable microspheres from about 0.1 to about 10 microns in diameter, to form said pharmaceutical composition.

30. The method of claim 29 wherein said dilution of albumin with dextrose is a 3-fold dilution.

31. The method of claim 29 wherein said human serum albumin is a 5% by weight solution.

32. The method of claim 29 wherein said dextrose is a 5% by weight solution.

33. The method of claim 19 wherein said microbubble composition comprises:
   microbubbles enhanced with an insoluble gas wherein said gas is encapsulated in a protein-coated shell.

34. The method of claim 33 wherein said insoluble gas is a perfluorocarbon gas.

35. The method of claim 34 wherein said perfluorocarbon gas is selected from the group consisting of perfluoromethane, perfluoroethane, perfluoropropane, perfluorobutane and perfluoropentane.

36. The method of claim 35 wherein said perfluorocarbon gas is perfluorobutane.

37. The method of claim 35 wherein said perfluorocarbon gas is perfluoropropane.

38. A method for converting animals out of fibrillation comprising:
   introducing a microbubble composition to said animal by intravenous injection so that said composition will perfuse the heart, a pharmaceutical composition comprising a microbubble ultrasound contrast agent, and thereafter;
   applying transthoracic high mechanical index ultrasound to said heart of a portion thereof.

* * * * *

UNITED STATES PATENT AND TRADEMARK OFFICE
CERTIFICATE OF CORRECTION

PATENT NO.    : 6,439,236 B1
DATED         : August 27, 2002
INVENTOR(S)   : Porter et al.

It is certified that error appears in the above-identified patent and that said Letters Patent is hereby corrected as shown below:

Column 1,
Lines 7-9, should read:
-- Work for this invention was funded in part by a federal Grant from NIH, Grant H61158. The Government may have certain rights in this invention. --.

Signed and Sealed this

Sixth Day of September, 2005

JON W. DUDAS
*Director of the United States Patent and Trademark Office*